United States Patent [19]

Bercovici et al.

[11] Patent Number: 4,701,328
[45] Date of Patent: Oct. 20, 1987

[54] COMPOSITIONS FOR FEEDING ANIMALS

[75] Inventors: Daniel Bercovici, Nice; Hubert Gaertner; Antoine Puigserver, both of Marseilles, all of France

[73] Assignee: A.E.C. Societe de Chimie Organique et Biologique, Commentry, France

[21] Appl. No.: 824,470

[22] Filed: Jan. 31, 1986

[30] Foreign Application Priority Data

Feb. 1, 1985 [FR] France .................................. 85 01418

[51] Int. Cl.$^4$ .......................... A23K 1/00; A23K 1/22
[52] U.S. Cl. ........................................ 426/2; 426/623; 426/656; 426/807
[58] Field of Search .................... 426/2, 623, 656, 807; 528/328

[56] References Cited

U.S. PATENT DOCUMENTS

| 3,350,365 | 10/1967 | Wakasa et al. | 528/328 |
| 4,289,872 | 9/1981 | Denkewalter et al. | 528/328 |
| 4,385,169 | 5/1983 | Kato et al. | 528/328 |
| 4,590,260 | 5/1986 | Harada et al. | 528/328 |

FOREIGN PATENT DOCUMENTS 0015668 of 1980 European Pat. Off. ............ 426/656

OTHER PUBLICATIONS

Gaertner et al., "Covalent Attachment of Poly L-methionine to Food Proteins for Nutritional & Functional Improvement", J. Aque Food Chem. (1984), pp. 1371-1376.

Hirschmann et al., "The Controlled Synthesis of Peptides in Aqueous Medium", J. Am. Chem. Soc., vol. 93, (1971), pp. 2746-2754.

Primary Examiner—R. B. Penland
Attorney, Agent, or Firm—Stevens, Davis, Miller & Mosher

[57] ABSTRACT

Polylysine and/or polymethionylpolylysine are advantageously incorporated in compositions for feeding animals, especially ruminants, to provide assimilable lysine and methionine.

5 Claims, No Drawings

COMPOSITIONS FOR FEEDING ANIMALS

The present invention relates to compositions for feeding animals containing lysine, or methionine and lysine in assimilable form.

Lysine and methionine are essential amino acids which promote animal growth and it is frequently necessary to supplement animal feed stuffs with compositions which contain one or both of these amino acids and which release the amino acid in the animal. In the case of ruminants, for these amino acids to be able to exert their beneficial effect, it is important that they should be given in a form which is stable in the rumen and releases the amino acids or assimilable oligopeptides in the intestine.

We have now found that animal feeds can be supplemented with lysine and/or methionine in the form of polylysine and/or polymethionylpolylysine.

The invention accordingly provides animal feed compositions comprising polylysine and/or polymethionylpolylysine. The invention further provides a method of feeding an animal which comprises supplying the said animal with a diet including a sufficient amount of polylysine, polymethionylpolylysine or both to provide a diet containing substantially all the said animal's dietary requirements of lysine, or lysine and methionine.

The polylysines and polymethionylpolylysines which can be used in the invention generally have a molecular weight of 1,000 to 1,000,000 daltons, and preferably 20,000 to 200,000 daltons.

The polylysines can be obtained by polymerization of $N^\epsilon$-carbobenzoxylysine N-carboxyanhydride in an organic solvent such as dioxane in the presence of an aprotic base such as sodium methylate or of diethylamine, which performs the role of initiator, at a temperature in the region of 20° C. Control of the ratio between the initiator and the lysine derivative employed enables the molecular weight of the polymers formed to be varied.

The N-carbobenzoxy protective groups can be removed by the technique of Ben Ishai and Berger (J. Org. Chem. 17, 1564–1570, 1959) using hydrobromic acid in acetic acid. The precipitated polylysine is separated and then purified by dialysis after it has been dissolved in water. The polylysine is separated by lyophilization of its aqueous solution. With the polymer thereby obtained, it is possible to monitor the removal of the protective group (by conversion to α-amino-ε-hydroxy-caproic acid by hydrolysis with trypsin). The molecular weight of the polylysine obtained can be determined from the sedimentation coefficient measured by analytical ultracentrifugation, or by measuring the specific viscosity.

Polymethionylpolylysine can be prepared by the reaction of methionine N-carboxyanhydride with polylysine according to the method of Gaertner and Puigserver (J. Agric. Food Chem. 32, 1371–1376, 1984) for preparing polymethionyl proteins.

The reaction of methionine N-carboxyanhydride with polylysine can be performed at a pH between 6 and 11, in a bufferred medium and using methionine N-carboxyanhydride in molar excess with respect to the lysine residues. The reaction is generally performed at a temperature in the region of 4° C.

The use of methionine N-carboxyanhydride at a pH of about 6, for example 6.5, promotes the polymerization of this amino acid onto the amino groups of the polymer. In this case, methionine N-carboxyanhydride is generally used in a molar excess of between 1 and 5 with respect to the lysine residues.

When working at a pH in the region of 11, for example 10.2, it is preferable to proceed by successive additions of methionine N-carboxyanhydride, to obtain a better distribution of the grafted methionine residues. Between each addition of the reagent, using on each occasion a molar excess of reagent of between 1 and 1.5 relative to the lysine residues, the reaction mixture is brought to room temperature and its pH is lowered to about 3–4, to enable decarboxylation of the intermediate carbamate to take place and enable further binding of the reagent to the free amino groups to occur.

The excess methionine N-carboxyanhydride in relation to the free amino groups of the polylysine permits determination of the relative proportion of methionine and lysine in the finished product. The methionine/lysine ration is generally between 0.4 and 4.

Polymethionylpolylysine may be isolated by lyophilization of its aqueous solution, which has been dialysed beforehand.

The N-carbobenzoxylysine and methionine N-carboxyanhydrides used for the preparation of the polymers used in the invention can be prepared by the method of Hirschman et al. (J. Amer. Chem. Soc. 93, 2746–2754, 1971), by the action of anhydrous phosgene on a suspension of the amino acid in an inert organic solvent such as anhydrous tetrahydrofuran, at a temperature of 30° to 60° C., preferably about 45° C.

The Examples which follow illustrate the preparation of the polymers used in the invention.

EXAMPLE 1

N-Carboxybenzoxy-L-lysine N-carboxyanhydride polymerizes in the presence of an initiator (sodium methylate), working in dioxane at 20° C. The disappearance of the monomer from the reaction medium enables its polymerization to be followed. Polymerization is complete after 75 hours. The polymer obtained takes the form of a viscous product.

The polymer is treated with acetic acid saturated with hydrobromic acid for 30 minutes. The precipitate formed is washed with diethyl ether and dried. After solubilization in water followed by dialysis, the poly-L-lysine obtained is separated from its solution by lyophilization. The molecular weight is in the region of 290,000 daltons.

Deamination of the poly-L-lysine enables the presence of the free amino groups to be verified. After acid hydrolysis, chromatographic analysis reveals a single peak corresponding to the presence of α-amino-ε-hydroxy-caproic acid.

N-Carbobenzoxy-L-lysine N-carboxyanhydride is obtained by bubbling anhydrous phosgene into a suspension of $N^\epsilon$-carbobenzoxy-L-lysine in anhydrous tetrahydrofuran at 45° C. When the reaction is complete, bubbling with anhydrous nitrogen removes excess phosgene. After evaporation of the solvent, the product is dissolved in ethyl acetate. The solvent is evaporated and the residue taken up with ethyl acetate. The operation is repeated twice. N-Carbobenzoxy-L-lysine N-carboxyanhydride crystallizes on slow addition of N-hexane to its solution in ethyl acetate, up to a 1:1 ratio (by volume). The crystals obtained are washed with a hexane/ethyl acetate (9:1 by volume) mixture; they melt at 97° C.

EXAMPLE 2

Poly-L-lysine in solution at 5 mg/cm$^3$ in sodium phosphate buffer (100 mM) at pH 6.5 containing 150 mM sodium chloride is maintained at 4° C. With vigorous agitation and with the pH maintained constant by adding 0.1 N sodium hydroxide, 1 mole of methionine N-carboxyanhydride is added per lysine residue. After the mixture has been left overnight at 4° C., the product is dialysed against water for 3 days, and the solution is then lyophilized.

The poly-L-methionylpoly-L-lysine obtained has a methionine/lysine ratio of 0.55, and contains 27% of modified lysine residues. The binding yield is in the region of 80%.

L-Methionine N-carboxyanhydride, which takes the form of an oily product, is obtained by the action of phosgene on L-methionine under the conditions described above for obtaining N-carbobenzoxy-L-lysine N-carboxyanhydride.

EXAMPLE 3

Using the procedure of Example 2, but with 3 moles of L-methionine N-carboxyanhydride per Lysine residue, a poly-L-methionylpoly-L-lysine is obtained in which the methionine/lysine ratio =1.90 and which contains 49% of modified lysine residues.

EXAMPLE 4

Using the procedure of Example 2, but with 5 moles of L-methionine N-carboxyanhydride per lysine residue, a poly-L-methionylpoly-L-lysine is obtained in which the methionine/lysine ratio =3.40 and which contains 70% of modified lysine residues.

EXAMPLE 5

Poly-L-lysine is dissolved at 4° C. in buffered sodium bicarbonate solution (100 mM) at pH 10.2 containing 150 mM sodium chloride. 1 mole of L-methionine N-carboxyanhydride is added per lysine residue. The temperature is allowed to rise to 20° C. and the pH of the reaction mixture is adjusted to pH 3-4 for 10 minutes. After being cooled to 4° C., the product is dialysed against distilled water for 3 days, and the solution is then lyophilized.

A poly-L-methionylpoly-L-lysine in which the methionine/lysine ratio =0.45, and which contains 45% of modified lysine residues, is thereby obtained.

EXAMPLE 6

Using the procedure of Example 5, but with 1.2 mole of L-methionine N-carboxyanhydride per lysine residue, a poly-L-methionylpoly-L-lysine is obtained in which the methionine/lysine ratio =0.53 and which contains 50% of modified lysine residues.

EXAMPLE 7

Using the procedure of Example 5, but with 3 times 1 mole of L-methionine N-carboxyanhydride per lysine residue, a poly-L-methionylpoly-L-lysine is obtained in which the methionine/lysine ratio =2.10 and which contains 66% of modified lysine residues.

The availability of the lysine and methionine in the polymers used in the invention can be demonstrated in vitro by successive digestions using enzymes present in the digestive tract, such as pepsin, pancreatic juice and intestinal aminopeptidase. Table I shows the relative amounts of lysine and methionine released during digestion:

TABLE I

| PRODUCT OF EXAMPLE | METHIONINE/ LYSINE RATIO | METHIONINE RELEASED % | LYSINE RELEASED % |
|---|---|---|---|
| 2 | 0.55 | 45 | 44 |
| 3 | 1.90 | 63 | 53 |
| 4 | 3.40 | 18 | 5 |
| 5 | 0.45 | 56 | 54 |
| 6 | 0.53 | 54 | 60 |
| 7 | 2.10 | 2 | 5 |

Depending on the type of polymer used, the availabilites of the two amino acids are very variable. In general, the products obtained by polymerization at pH 6.5, which have a relatively high methionine content (Example 3) are readily hydrolysed, whereas the products obtained at pH 10.2, which are characterized by a substantial proportion of modified lysine residues (Example 7) are less accessible to the proteolytic enzymes. Moreover, the polymers obtained at pH 6.5, which contain a substantial proportion of modified lysine residues, are more readily hydrolysed than those obtained at pH 10.2 by successive additions of methionine N-carboxyanhydride.

In general, satisfactory availability is obtained when the methionine/lysine ratio is less than 2, and preferably about 1, this ratio being variable according to the process used for producing the polymethionylpolylysine.

The nutritional value of the polymethionylpolylysine used in the present invention has been demonstrated in rats receiving a basic diet deficient in lysine and methionine. The basic diet (hereinafter designated UAR) comprised:

Wheat gluten (50% protein) 10%
Vegetable oil 5%
Starch 50%
Dentrose 25%
Essential Minerals 4%
Vitamins 0.5%
Trytophane 0.3%
Methionine and Cysteine 0.25%
Lysine 0.28%
The balance being absorbed water.

For example, using poly-L-lysine (as described in Example 1) and a poly-L-methionylpoly-L-lysine in which the methionine/ lysine ratio is in the region of 1 (0.85), and which contains 30% of modified lysine residues (obtained in the way described in Example 2 using 1.3 moles of L-methionine N-carboxyanhydride per lysine residue), the results collated in Table II have been obtained.

TABLE II

| FEEDING DIET | FEED INTAKE g/14 DAYS | PROTEIN INTAKE g/14 DAYS | WEIGHT GAIN g/14 DAYS | COEFFICIENT OF PROTEIN EFFICIENCY |
|---|---|---|---|---|
| UAR | 208.9 ± 27.5 | 20.89 ± 2.75 | 41.30 ± 5.20 | 1.98 ± 0.12 |
| UAR + Met + Lys (both free) | 189.6 ± 28.1 | 20.67 ± 3.06 | 52.15 ± 13.00 | 2.67 ± 0.35 |

TABLE II-continued

| FEEDING DIET | FEED INTAKE g/14 DAYS | PROTEIN INTAKE g/14 DAYS | WEIGHT GAIN g/14 DAYS | COEFFICIENT OF PROTEIN EFFICIENCY |
|---|---|---|---|---|
| UAR + Met (free) + poly-L-lysine | 227.9 ± 26.9 | 25.30 ± 2.99 | 72.30 ± 8.70 | 2.86 ± 0.14 |
| UAR + POLY-L-METHIONYL-POLY-L-LYSINE | 197.1 ± 23.0 | 21.90 ± 2.56 | 55.60 ± 10.60 | 2.52 ± 0.25 |

The data in this table show that supplementation of the basic diet with free lysine and free methionine significantly improves the growth of the animals, and that the growth of animals fed with a diet supplemented with poly-L-methionylpoly-L-lysine is not significantly different from that of animals whose diet is supplemented with free amino acids. Furthermore, supplementation with lysine in the form of poly-L-lysine is significantly more efficient than with lysine in free form.

The polymethionylpolylysine used in the present invention possesses the exceptional property of being soluble in the rumen of ruminants while withstanding bacterial degradation. For examples, poly-L-methionyl-poly-L-lysine (0.5 g) can be introduced in nylon sachets having a mesh aperture size of 300×300 u. The sachets are incubated for 48 hours in the rumen of fistulated ewes. The sachets are then recovered and washed. The remaining active substance is determined quantitavely by a suitable method. The amounts of L-lysine and L-methionine found in the nylon sachets correspond, respectively, to 80 and 60% of the initial contents. When L-lysine and L-methionine are taken in free form, only a small proportion of these amino acids escapes microbial fermentation.

The polymethionylpolylysine used in the invention is therefore an adjuvant of choice for feeding ruminants.

The compositions of the invention for feeding animals contain a sufficient amount of polylysine and/or polymethionylpolylysine.

The polymethionylpolylysine can be distributed as a uniform dispersion in a complete compound feed. It can also be distributed in supplementary feeds, most frequently with other additives such as vitamins and mineral salts. These supplementary feeds can be either mixed with the feed ration, or eaten as they are. They customarily represent 5 to 20% of the feed ration.

The "premixes", used for preparing the supplementary feeds or complete feed rations, generally contain from 1 to 20% of polymethionylpolylysine. They constitute a convenient intermediary which facilitates the uniform distribution of the adjuvant in the feeds.

The "premixes" themselves are generally obtained from concentrates which contain from 99.9 to 20% of polymethionylpolylysine, to which edible denaturants such as feed dyes, flavourings, dispersants or anti-agglomerants and feed fillers are added.

The concentrates and premixes are generally pulverulent. The supplementary feeds and complete compound feeds can be either pulverulent or in the form of pellets prepared by the customary techniques.

We claim:

1. An animal feed composition consisting essentially of a complete compound feed or supplemental feed together with polylysine in which at least some of the amino groups of the polylysine have been grafted with polymethionine and in which the ratio of methionine to lysine is less than 2, the resultant polymethionylpolylysine having a molecular weight of 20,000 to 1,000,000 daltons, and the amount of said polymethionylpolylysine being sufficient to provide a diet containing substantially all of the animal's dietary requirements of lysine and methionine.

2. A composition according to claim 1, in which the lysine and methionine are in L-form.

3. A composition according to claim 1 in which the polymethionylpolylysine has a molecular weight of 20,000 to 200,000.

4. A composition according to claim 1 in which the methionine/lysine ratio is from about 0.4 to about 2.

5. A method of feeding a ruminant animal which comprises supplying the said animal with a basic diet including a sufficient amount of polylysine in which at least some of the amino groups have been grafted with polymethionine and in which the ratio of methionine to lysine is less than 2, the resultant polymethionylpolylysine having a molecular weight of 20,000 to 1,000,000 daltons, to provide a diet containing substantially all the said animal's dietary requirements of lysine and methionine.

* * * * *